US006544214B1

United States Patent
Utterberg

(12) United States Patent
(10) Patent No.: US 6,544,214 B1
(45) Date of Patent: Apr. 8, 2003

(54) SUBCUTANEOUS ACCESS NEEDLE AND METHOD

(75) Inventor: David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/318,419

(22) Filed: May 25, 1999

(51) Int. Cl.⁷ .............................................. A61M 11/00
(52) U.S. Cl. .................................... 604/93.01; 604/272
(58) Field of Search ............................. 604/93.01, 272, 604/264, 244, 265, 183, 242, 175, 164.01, 164.04, 164.1, 164.11, 164.12, 164.13

(56) References Cited

U.S. PATENT DOCUMENTS

| | | | |
|---|---|---|---|
| 4,955,861 A | | 9/1990 | Enegren et al. |
| 5,002,557 A | * | 3/1991 | Hasson ........................ 606/191 |
| 5,071,413 A | | 12/1991 | Utterberg |
| 5,139,486 A | * | 8/1992 | Moss .......................... 604/164 |
| 5,263,930 A | * | 11/1993 | Ensminger ................... 604/93 |
| 5,322,516 A | * | 6/1994 | Brugger ...................... 604/192 |
| 5,348,542 A | | 9/1994 | Ellis ........................... 604/173 |
| 5,453,094 A | * | 9/1995 | Metcalf et al. ............. 604/164 |
| 5,562,617 A | | 10/1996 | Finch, Jr. et al. |
| 5,873,854 A | * | 2/1999 | Wolvek ....................... 604/104 |

FOREIGN PATENT DOCUMENTS

| | | |
|---|---|---|
| WO | WO 97/47338 | 12/1997 |
| WO | WO 98/31416 | 7/1998 |
| WO | WO 99/03527 | 1/1999 |

* cited by examiner

Primary Examiner—Anhtuan T. Nguyen
Assistant Examiner—Ann Y Lam
(74) Attorney, Agent, or Firm—Garrettson Ellis; Seyfarth Shaw

(57) ABSTRACT

A cannula is provided for connection with an implanted artificial port through a preformed needle track through the skin of a patient. The port has a flow conduit to connection with the body lumen and the closure member for blocking flow between the port and the body lumen. The closure member is normally closed, but openable by an insertion of a properly sized cannula into the port. The first cannula has a proximal end which is connected to a hub, a proximal portion adjacent to the proximal end, and a distal portion. The distal portion is of insufficient size to open the closure member when inserted into the port, so that the first cannula may be used for flushing the implanted port interior and the needle track with disinfectant solution. The proximal portion is of larger diameter than the distal portion and is proportioned to dilate the needle track to facilitate subsequent advancement of a larger diameter fluid flow cannula through the needle track after withdrawing of the first cannula. The larger, fluid flow cannula is of a size sufficient to open the closure member to obtain communication with the body lumen.

26 Claims, 3 Drawing Sheets

SUBCUTANEOUS ACCESS NEEDLE AND METHOD

BACKGROUND OF THE INVENTION

In the field of hemodialysis and other forms of blood processing, the various techniques for gaining access to the blood stream of a patient have exhibited significant, known, technical disadvantages.

In response to this, a new technology for blood access has been developed by Vasca Inc. of Topsfield, Mass., involving an implantable port chamber in the body of a patient which is used in a manner described in PCT Publications WO98/31416 and WO99/03527, as well as in other references. Specifically, an implanted port is implanted within the skin of the patient, with a preformed needle track or "tract" extending from the entrance of the port through the tissue and through the skin. Thus, repeated penetration of the needle or tissue "tract" by an access cannula can take place without cutting of tissue, since cells similar to scar tissue form around the walls of the tissue tract, providing a result similar to the tissue track passing through earlobes in the case of pierced ears.

A Vasca or other type of implanted port communicates with a body lumen, typically a vein of the patient, but desirably with a valve that normally closes the flow path between the implanted port and the vein of the patient. When access to the blood stream is desired, (or access to another body lumen), a needle penetrates the preformed tissue "tract" and passes into the entrance of the port, pushing open the closure valve and thus providing access to the blood stream through the port.

It has been found to be usually desirable to also provide a flush treatment of the port interior and the tissue track leading to the skin.

This is accomplished in the prior art with a thin needle, thinner than the access needle that opens the port valve to gain access for extracorporeal blood flow, so that the thin needle enters the implanted port through the preformed tissue track without pushing open the valve. Then, flushing/disinfectant solution may pass into the port through the thin needle, with the flushing solution flowing outwardly through the tissue track along the exterior of the thin needle, to provide antibacterial flushing of the implanted port and tissue track.

The tissue track is preferably formed by a sharp needle, so that, when closed and not containing a needle, it is of the cross-sectional shape of a slit, and preferably a crescent-shaped slit, and not a round hole like a pierced ear. This provides natural sealing without substantial bleeding, after the tissue track has formed its scar tissue wall, especially in the circumstance where the tissue track leads to an implanted, valved port so that little or no blood backflow occurs when needles are withdrawn from the tissue track.

It has been found to be generally desirable for the disinfection procedure using a narrow needle to be used with every procedure of access to the tissue track. Thus it is desirable for the disinfecting needle and a needle that facilitates the dilation and stretching of the tissue track for receiving of blood access needle to work together in concert.

While dull access needles have been taught for use with preformed tissue tracks, clinical experiences show to the present that only certain types of dull access needles have been able to access such tracks, which are also called "buttonholes". Needles that have too steep a bevelled tip angle, or no bevel at all with a perpendicular, flush end, generally cannot spread apart the freshly formed tissue track after a few days of nonuse, and cannot be used to gain entry unless a trocar is used in conjunction with them. However, trocars are expensive, and are difficult to place in non-gapped relation to the overlying cannula. If a gap occurs, the resulting incision can be painful when it tears tissue along the needle track. Nevertheless, the use of dull needles is highly desirable in view of laws that are going into place in the various states of the United States and perhaps elsewhere, mandating the use of either dull needles or guarded needles, to avoid accidental needle stick.

Thus, it would be desirable for a dull, safe needle to be used to pre-dilate the buttonhole so that a subsequent dull, safe, large-port access cannula, for example a dialysis flow cannula, can be inserted without a trocar. It would be beneficial if such a predilation needle can serve as a disinfecting needle as well, so that two functions may take place: a pre-dilation of the tissue track so that a blunt, larger needle can penetrate the track, and also providing of effective antimicrobial flushing for reduction of infection in the tissue track.

By this invention, such a needle or cannula, and a method of use, is provided to address the above disadvantages and technical issues.

DESCRIPTION OF THE INVENTION

By this invention, a cannula set has a first cannula for entry at least partially into an implantable artificial port through a preformed needle track through the skin of a patient, for fluid flow access in either direction. The implantable port has a flow conduit for connection with a body lumen such as a vein of a patient, plus a closure member (valve) for blocking flow between the port and the body lumen. This may comprise a moveable clamp which opens and closes a flexible tubing which typically is grafted at one end to a vein of a patient and which connects with the lumen of the implantable port at the other end. The closure member is normally closed by spring action or alternatively closures such as that disclosed by ports of Ensminger, Prosl and others, which closures are openable by insertion of a properly-sized and shaped cannula into the port.

The first cannula of this invention has a proximal end which maybe is connected to a hub, a proximal portion adjacent to the proximal end, and a distal portion. The distal portion of the first cannula is of insufficient size to open the closure member when inserted into the port, for example by being of insufficient length, or of insufficient outer diameter, to actuate the closure member.

The proximal portion of the first cannula may be of larger outer diameter than the distal portion, and is proportioned to dilate the tissue surrounding the preformed needle track leading to the implanted port, to facilitate subsequent advancement of a larger diameter fluid flow cannula through the needle track after withdrawing the first cannula.

Thus, the first cannula may be passed through the needle track to engage the implanted port with the distal cannula portion without causing the closure member of the port to be opened. Flushing/disinfectant solution may then be passed into the system through the first cannula, with the result that the flushing solution flows outwardly from the port through the port interior and the needle track outside of the first cannula, to provide a disinfection and flushing of both the interior of the implanted port and the needle track, for suppression of infection. Simultaneously, the proximal portion of the first cannula stretches the tissue surrounding the preformed needle track so that, upon withdrawal, it becomes a easier matter to insert a larger, second cannula through the needle track into engagement with the implanted port. This larger, second cannula is of sufficient size to cause opening of the closure member, so that the interior of the implantable port enters into fluid flow contact with the body lumen, particularly a vein of the patient. Thus, a relatively large diameter flow access path is provided through the port and the second cannula between the patient body lumen and the exterior. In the case of hemodialysis, this permits access to the venous system of the patient, so that blood can be withdrawn from the patient, passed through a blood processing apparatus such as a hemodialyzer, hemofiltration device, or the like, and then returned again to the patient, typically by means of a second implanted port and cannula system.

Preferably, especially for purposes of hemodialysis, hemofiltration, and the like, the first cannula may be at least 15 mm. in length. Also, the proximal portion of the first cannula, typically for purposes of hemodialysis or related technologies, may have an outer diameter of about 1.2 to 2.7 mm. and the distal portion may have an outer diameter of about 0.5 to 1.5 mm. The distal portion of the first cannula of this invention has preferably one half or less diameter of the specific proximal portion utilized.

Preferably for use in hemodialysis, hemofiltration, or the like the maximum diameter of the proximal portion of the first cannula is at least 70% of a minimum outer diameter of the second cannula which is for providing fluid flow through the tissue track to and from the patient.

Preferably, for hemodialysis, hemofiltration, and the like, the proximal portion of the first cannula will have a length of at least about five millimeters, which comprises at least a substantial portion of the length of the tissue track, for pre-dilation thereof preparatory to receiving the second fluid flow cannula.

As stated, the first cannula distal portion is preferably small enough to penetrate an implanted port which has a valve (closure member) so that the distal end can enter into the port without opening the valve. Typically the distal portion has a length of about 5 mm. or more, specifically a length sufficient to penetrate into the port without opening the valve as the proximal portion of the first cannula provides pre-dilation to the tissue tract. The first cannula and hub are typically connected to a syringe, or a length of tubing, connected to or carrying a source of disinfectant solution which is capable of use for flushing of the needle track and preferably the interior of the implanted port. Thus, as the pre-dilation of the needle track takes place, a flushing step may also be provided in which typically an antibacterial solution is used, flushing the interior of the port and the walls of the tissue track while the port valve is closed. Thus the connected vascular system or other body lumen of the patient is not subjected to contact with the disinfectant solution.

The first cannula may further define a frustoconical transition portion between the proximal and distal portions.

Each of the proximal and distal portions of the first cannula may typically be cylindrical or oval in cross-section, or either of them may be tapered in a typically conical shape from proximal larger ends to distal smaller ends, as may be desired.

Preferably, the distal end of the first cannula is blunt, so that it can penetrate through the tissue track without cutting tissue. Preferably, the distal end of the first cannula may be bevelled or otherwise pointed, but it remains blunt enough to be effectively incapable of cutting through intact, typical human skin at forces of less than 100 grams. As a specific test, the cannula of this invention preferably cannot penetrate a single thickness of DuPont Linear Density Polyethylene Sclairfilm of 0.004 inch (essentially 0.1 mm.) thickness at a pressure of 70 grams, as a test for preferred bluntness in accordance with this invention. Such cannulas do not generally penetrate human skin in typical circumstances where accidental needle sticks may take place.

After the flushing and pre-dilation of the needle or tissue track has taken place, the first cannula can be withdrawn, and a second cannula of greater width may be inserted into the tissue track. This cannula also is preferably blunt, and its easy entrance into the tissue track is effected by the pre-dilation which has taken place along with the antibacterial flushing provided by the first cannula. The second cannula serves as the conduit for blood flow for hemodialysis or the like, or other desired flow.

The second cannula has a relatively large inner diameter to facilitate high blood flow rates. Also, it may be desired for the second cannula to have an inward taper between its proximal end and a distal end so that the distal end is of less diameter than the proximal end, to permit easy access through the tissue track, while allowing the maximum possible blood flow rate.

Further in accordance with this invention, a method is used for providing access through the skin of the patient for communicating with a body lumen of the patient, which method comprises the following:

A first cannula having a non-cutting forward end is advanced through a pre-formed needle track ("buttonhole") through the skin of a patient, without significantly cutting tissue of the patient, while dilating at least most of the needle track with the cannula to a diameter that is about 70 to 125 percent of the minimum diameter of a subsequent cannula, but preferably no more than 100 percent. The first cannula is then removed. The second, subsequent cannula is then advanced through the dilated needle track into flow communication with the patient body lumen.

While this may be accomplished by direct communication through a "buttonhole" into a blood vessel of the patient or other body lumen, it is preferable for the subsequent cannula to be advanced into flow communication with a body lumen by engagement with an implanted artificial port, for example an artificial port as described in the previously cited PCT publications. Preferably, the first cannula, as before, has a distal portion of less outer diameter than the first cannula proximal portion, with the proximal portion being positioned in the needle track for dilating it. The distal portion, in this position of needle track dilation, penetrates the implanted port without opening a closure valve that separates the port from the body lumen. Then, prior to removal of the first cannula, one preferably passes flushing liquid through the first cannula, most of which liquid then passes out of the patient through the needle track, providing an antibacterial flushing effect for the suppression of infection.

Following this, the first cannula can be removed, and the second cannula inserted through the needle track into engagement with the artificial port.

The closure valve of the port opens with this larger diameter fluid flow needle, to permit abundant access to blood or other body fluids for extracorporeal processing thereof, as one use of this system, although an unlimited number of other medical uses are also contemplated, such as chemotherapy and other uses where percutaneous catheters are currently used.

Preferably in the field of hemodialysis, hemofiltration, etc., the second, access cannula is of a size of at least 14 gauge at its distal tip or larger, and, as previously stated, the second access cannula is preferably tapered so that its proximal end is larger than its distal end.

It is further preferable for the tapered second access cannula to have an angle of taper that matches a taper within an access port of the implanted port so that the cannula and the tapered access port wall can form a seal which is easily made with low connection pressures, and which is also easily broken when it is desired to remove the cannula, while reliable sealing in the manner of a luer connection may be achieved.

The respective first and second cannulas and their connected sets may be packaged in a kit or kits incorporating one or both of the cannula sets in a single package, a device for infusion through the first cannula such as a syringe, disinfecting material, gauze tape, and the like.

If desired, the first cannula may be replaced by a solid trocar having a similar shape so that a forward portion having a dull point may enter the port without opening a valve while a proximal portion of increased or increasing diameter permits pre-dilation of the tissue track for subsequent reception of the second, access cannula. The second, access cannula may be threaded around the trocar as the trocar is advanced. The trocar is of course withdrawn before the system is used, for access to body fluid such as blood.

DESCRIPTION OF SPECIFIC EMBODIMENTS

Figure 1:
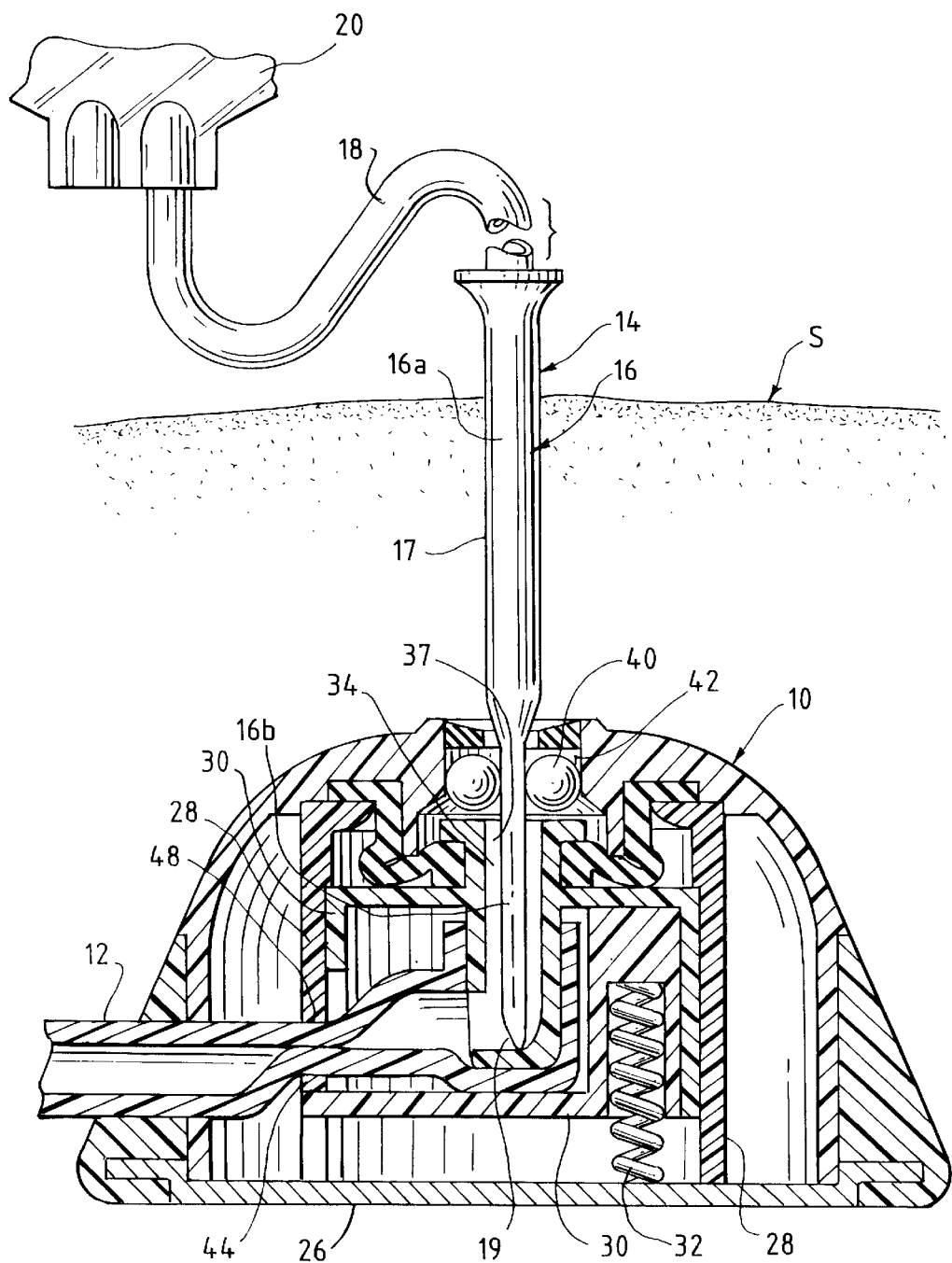
FIG. 1 is a substantially sectional view of an implanted artificial port for communication with the vascular system of a patient, shown to be in connection with a cannula of this invention, the cannula having a proximal end that is connected to a source of flushing solution.

Referring to FIG. 1, a longitudinal sectional view of an artificial port 10 is shown, the port being implanted below the skin S of a patient in a permanent manner. Port 10 is similar in its structure to the corresponding implantable port disclosed in PCT Publication WO98/31416 of Vasca Inc., the disclosures of which are incorporated by reference herein.

Implanted port 10 carries flexible tubing 12, which communicates in this embodiment with a vein of the patient by a surgical graft so that port 10 has access to the vascular system of the patient.

A cannula set 14 is provided, shown to have a cannula 16 which penetrates through the skin S to pass through a preformed tissue track (or tract) 17 to enter port 10 as shown in FIG. 1. Cannula set 14 also comprises in this embodiment a length of tubing 18 which connects with a source of flushing/disinfectant solution 20 such as a small solution bag. Alternatively, cannula set 14 may comprise cannula 16 in connection with a syringe which contains the flushing/disinfectant solution.

Cannula 16 comprises the "first cannula" described above, having a proximal portion 16a, which is proportioned to dilate needle track 17 from the original condition of the needle track 17, which is typically in the form of a slit. The walls of tissue track 17 typically carry scar tissue cells, so that as cannula 16 is advanced into needle or tissue track 17, there is little or no cutting of tissue. Cannula 16 has a blunt hor other non-cutting distal tip 19 to facilitate this. The predilation provided by proximal section 16a typically serves to prepare needle track 17 for further dilation with a second cannula which is typically of larger diameter than the diameter of proximal portion 16a. As will be described, the second, subsequent cannula is provided with the maximum practical inner diameter size. Particularly in the case of extracorporeal treatment of blood, it may be desirable to provide a high rate of blood flow through port 10 and the second cannula. Proximal portion 16a provides a desired predilation of tissue track 17, which facilitates the entrance of the still-larger second cannula to the tissue track after withdrawal of first cannula 16.

Cannula 16 also defines a distal portion 16b, which distal portion is of substantially reduced outer diameter compared with proximal section 16a. One purpose of this reduced diameter relates to the structure and functioning of implanted port 10, which will now be briefly described.

As stated, implanted port 10 communicates through a conduit 12, typically a flexible tubing, to a blood vessel of the patient such as a larger vein, or, if desired, some other body lumen such as the bladder, the liver, the lymphatic system, a body gland, or the like. Artificial body access port 10 has a multi-part housing 26 as shown, which carries a frame 28 in which actuator block 30 slides upwardly and downwardly, being biased in the upward position by spring 32. As taught in the cited international publication, actuator block 30 defines an axial bore 34 for receiving a needle or cannula. An upper mouth portion 37 of axial bore 34 defines a taper, with the upper mouth portion 37 being wider than the interior portion of bore 34.

Figure 2:
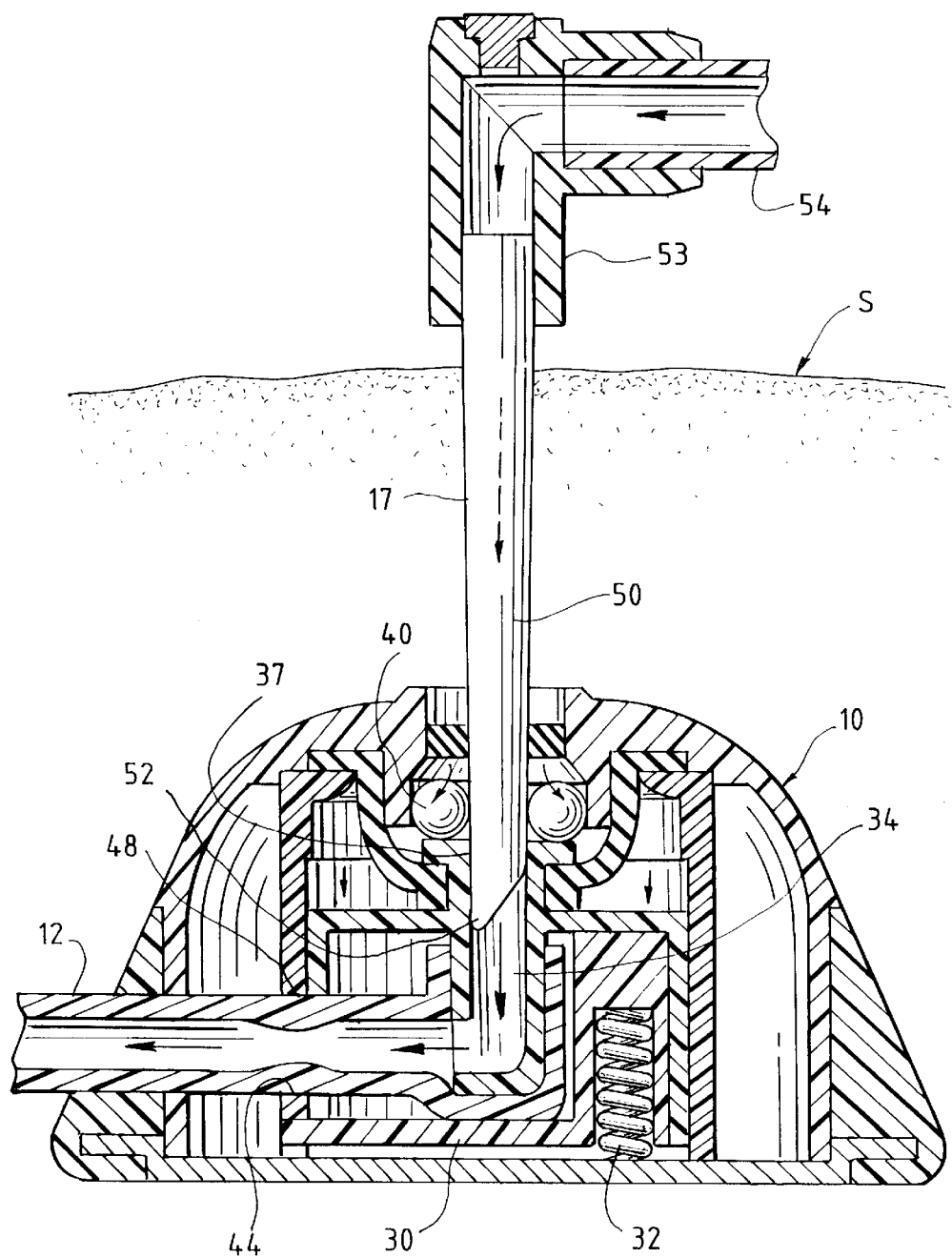
FIG. 2 is a substantially sectional view of the implanted artificial port as shown in FIG. 1, shown to be in communication with a second cannula for flow of blood or other solution to or from the patient.

Further as taught in the above cited international application, a pair or more of balls 40 are caged within a circular aperture 42 within housing 30 and communicating with axial bore 34. Balls 40 are shown in their elevated, normal position in FIG. 1, and in their depressed position in FIG. 2, being driven to depressed position when a needle of sufficient diameter is advanced to push the balls downwardly and then outwardly to the position shown, as discussed subsequently. Such pushing of the balls outwardly and downwardly causes depression of actuator block 30 downwardly, into the position shown in FIG. 2, which consequently depresses spring 32. By this act, tubing 12 is opened by the downward movement of pressure lip 44, away from upper lip 48, which is part of frame 28 that retains the moving actuator block 30 in its two positions. When such a larger diameter needle 50 of FIG. 2 is not in a position to spread balls 40, spring 32 causes actuator block 30 to rise to its upper position, with balls 40 moving inwardly and upwardly to a upper, constrained position, and as taught and illustrated in the cited international publication.

In the situation shown in FIG. 1, proximal portion 16b of cannula 16 is intentionally made of a diameter which is too little to drive balls 40 apart to a degree sufficient to effect opening of the closure of tube 12 found at walls 44 and 48. Thus, when that penetration is made as shown in FIG. 1, it is possible to flush interior portion 34 of implanted port 10, and also to flush the wall of tissue track 17 which surrounds proximal cannula portion 16a, with a desired flushing/disinfectant solution, which solution passes outwardly of the skin through tissue track 17, and provides antimicrobial action within port 10 and along the wall of tissue track 17. Thus, by the needle 16 of this invention, the predilation of tissue track 17, and the desired antimicrobial flushing of tissue track 17 and port 10, can be accomplished in one step, either with solution bag 10 or with a syringe without the use of tubing 18 and solution bag 20. Because the valve defined by walls 44, 48 remains closed, flushing/disinfectant solution does not find its way into the body during the flushing step.

If desired, a subsequent flush with isotonic saline or another appropriate solution may be provided to remove disinfectant.

First cannula 16 may have its proximal portion with an outer diameter of about 2 mm. and its distal portion 16b having an outer diameter of about 1 mm.

Then, first cannula 16 may be withdrawn, and replaced with second, fluid flow cannula 50 as in FIG. 2, which is shown to be typically of greater diameter at its smallest portion than the diameter of proximal portion 16a of the first cannula. Specifically, second cannula 50 is of conical structure having an angle of taper on each side of typically about one degree to four degrees, and preferably about 1.4–2.6 degrees, more specifically about 1.6–1.7 degrees, matching the angle of taper of conical passageway portion 37 of implanted port 10, so that a luer type conical seal may be provided between second cannula 50 and passageway 37 of implanted port 10.

If it is desired to reduce the torque and other pressures that are needed to break the tapered connection between the second cannula 50 and the inwardly tapering section 37 of the entrance conduit, the inward taper of the tapered cannula may have a taper that is essentially matched but slightly less (on the order of 0.1 degree) then the degree of taper of the inwardly tapering section 37 of the entrance conduit. In the circumstance, a reliable seal can be achieved that is more easily disconnected by twisting and removing of the cannula, when compared with the situation where the tapered cannula and the inwardly tapering section having exactly the same angle of taper. One can reduce this bonding strength of the tapered seal by increasing the difference between the inward taper of the tapered cannula from the degree of taper of the inwardly tapering section. One can also strengthen this bond by reducing the difference between the two tapered angles. Particularly, the tapered cannula 50 may preferably have a distal end 52 of 11–13 gauge, and an opposed, proximal end at hub 53 of 14–15 gauge, as measured by the conventional gauge measurement system used in the industry.

Each of cannulas 16 and 50 are preferably made of medically acceptable, rigid material, for example stainless steel or copolymer plastic.

Continuing to refer to FIG. 2, as the larger diameter second cannula 50 advances through tissue track 17 and the tapered channel 37 of port 10, its larger diameter is sufficient to drive balls 40 outwardly and downwardly, thus compressing spring 32 and depressing actuator block 30 to open the valve formed by walls 44, 48 as shown. Thus, second cannula 50 is in flow contact with the vascular system of the patient through tube 12 and the opened, implanted port 10. Thus, a flow of blood passes either inwardly or outwardly from the patient, as part of a blood flow circuit for extracorporeal blood processing, for example hemodialysis. Access to this circuit can be achieved without cutting of any tissue because of the presence of pre-cut tissue track 17, which may be healed and have a wall comprising cells of the type found in scar tissue, particularly as disclosed in PCT International Publication WO99/03527 of Vasca Inc.

At the end of the procedure, second cannula 50 is withdrawn, resulting in the spontaneous movement of balls 40 and actuator block 30 upwardly, resulting in the closing of the valve defined by walls 44, 48 again. Tissue track 17 closes up again without a large amount of bleeding, since access to the vascular system of the patient is blocked by the closed valve. Upon a subsequent penetration by another cannula through needle track 17, the cannula can pass through the track essentially without cutting of tissue or creating of bleeding, so that the pain is minimal and the risk of infection is lowered. Second cannula 50 may have a substantially blunt or other non-cutting distal end 52 to assure that little or no tissue is cut upon its passage through the tissue track 17.

Figure 3:
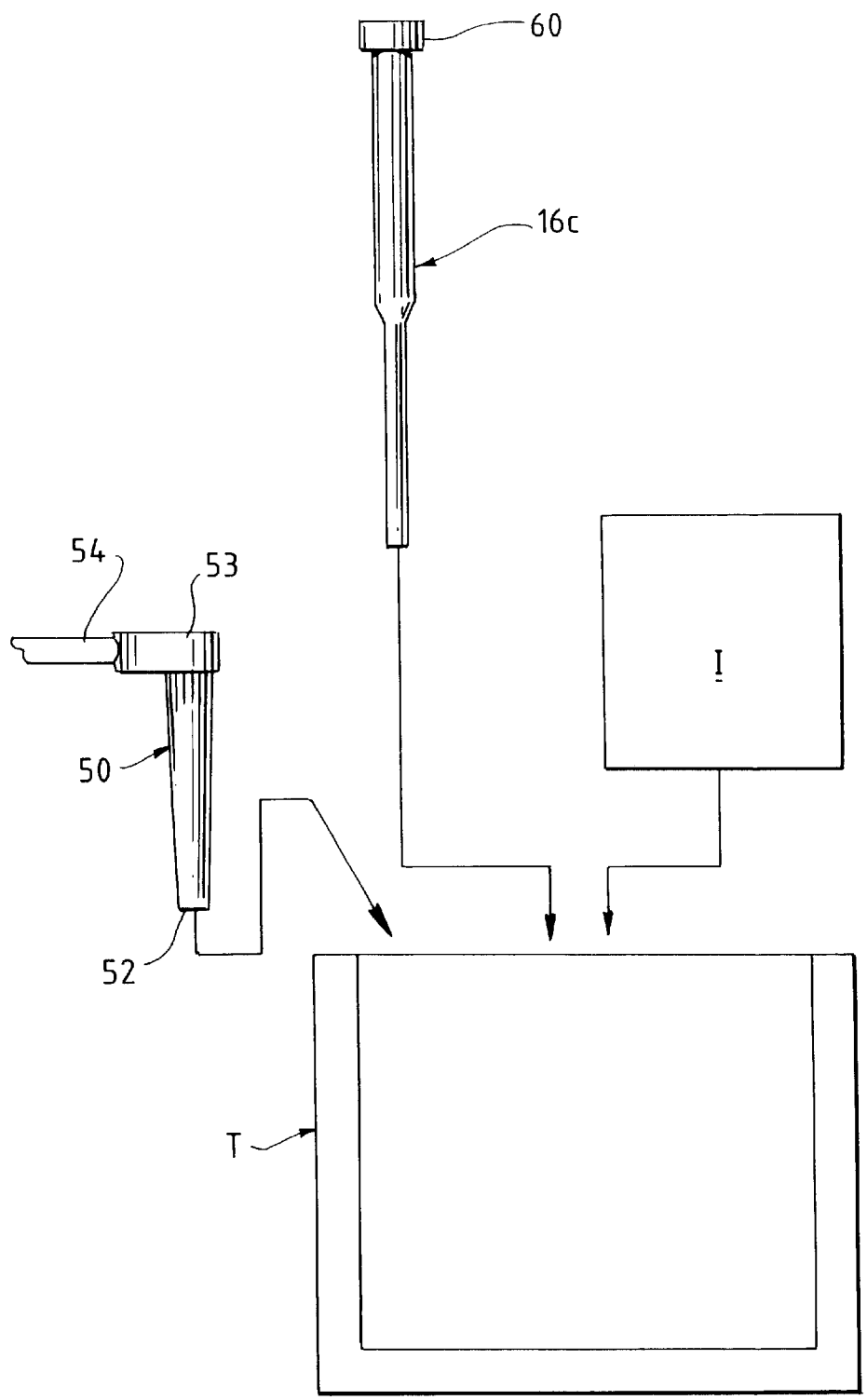
FIG. 3 shows a kit that incorporates the cannula sets of FIGS. 1 and 2, plus packaging and instructions.

Referring to FIG. 3, a kit is shown which comprises a package such as tray T, plus instructions I. Tray T carries the two cannulas 16c, 50 of the previous drawings and their attached sets. This particular cannula 16c may be of the design of cannula 16, except that hub 60 at the proximal end of cannula 16c is not connected to tubing, but is adapted to receive a syringe for application of the flushing/disinfectant solution to an implanted port as previously described, which syringe may be enclosed in tray T.

Second cannula 50, for flow communication to and from the body, and its hub 52 and attached set tubing 54, can also be provided in tray T, with the two cannulas being provided together, or separately in separate packages if desired. The remainder of tubing 54 may be of the conventional design of an arterial or venous blood flow set for hemodialysis, hemoperfusion, or any other design of tubular flow set for any desired medical procedure. Other desired pieces of equipment may also be provided in tray T if desired.

While the distal portion 16b of the first cannula 16 is shown to be narrower than the proximal portion, for the purpose of not actuating the closure valve in the particular implanted port 10 that is disclosed in FIG. 1, other modifications of the distal end of a first cannula may be made for the purpose of entering various designs of implantable ports without actuating a valve that permits the port to communicate with the connected body lumen of a patient. For example, with respect to the implantable port member of the BioLink Corporation as disclosed in PCT International Publication WO97/47338, the particular first cannula that could be used in accordance with this invention in conjunction with such an implanted port might have a distal portion that is too short to reach the valve found in that particular, implanted port. The second cannula, which is used for actual communication with the body, would be longer, thus passing through the valve into flow communication with a body lumen. Accordingly, the first cannula could be used to flush the interior of such an implanted port and the tissue track in a manner similar to the flushing procedure described above, without opening flow communication with the body interior.

The above has been offered for illustrative purposes only, and is not intended to limit the scope of the invention of this application, which is as defined in the claims below.

That which is claimed:

1. A combination cannula and artificial port comprising:
   an implantable artificial port having a flow conduit for connection with a body lumen and a closure member for blocking flow between the port and the body lumen, said closure member being normally closed but openable by insertion of a properly sized and shaped cannula into said port; and
   a first, substantially rigid predilation and disinfecting cannula for connection with the implantable artificial port through the skin of a patient, said first cannula having a proximal end, a proximal portion adjacent to said proximal end, a distal portion, and a frustoconical transition portion between the proximal and distal portions, said distal portion being of insufficient size to open said closure member when inserted at least partially into the port, said proximal portion being of larger diameter than said distal portion and being proportioned to dilate said needle track to facilitate subsequent advancement of a larger fluid flow cannula through said needle track after withdrawing said first cannula, said first cannula being connected to a source of solution for flushing and disinfecting of said needle track.

2. The cannula of claim 1 in which said first cannula is at least 15 mm. in length.

3. The cannula of claim 2 in which said proximal portion for the first cannula has an outer diameter of about 1.2 to 2.7 mm. and said distal portion has an outer diameter of about 0.5 to 1.5 mm.

4. The cannula of claim 1 in which said distal cannula portion has a blunt end.

5. The cannula of claim 1 in which said first cannula is connected to a source of disinfectant solution capable of use for flushing of said needle track.

6. The cannula of claim 1 in which said proximal and distal-portions are cylindrical.

7. A medical procedure kit which comprises:
   a first cannula set having a first, substantially rigid, predilation, disinfecting cannula for connection with an implantable artificial port through a preformed needle track through the skin of a patient, said first cannula having a proximal portion and a distal portion, said proximal portion being of larger diameter than said distal portion and being proportioned to dilate said needle track to facilitate subsequent advancement of a larger diameter blood flow cannula through said needle track after withdrawing said first cannula, said first cannula further defining a frustoconical transition portion between said proximal and distal portions and the distal portion having a diameter less than a diameter of a bore of the artificial port so that a gap is formed between a side of the cannula and the bore of the artificial port providing for disinfectant fluid to be passed through the cannula, into the artificial port, through the gap and through the tissue track so that the first cannula provides a dual function of dilating and flushing the needle track;
   a second cannula set which comprises a second blood flow cannula for providing access through the skin of a patient through said needle track, the proximal portion of said first cannula having a minimum outer diameter that is about seventy to one hundred twenty five percent of a minimal outer diameter of said second cannula; and
   packaging for both of said cannula sets.

8. The kit of claim 7 in which said second cannula comprises a proximal end connected to a second hub and a distal end, said second cannula tapering inwardly from the proximal to the distal end.

9. The kit of claim 8 in which said proximal and distal portions are cylindrical and the distal cannula end being blunt.

10. The kit of claim 9 in which said first cannula is connected to a length of tubing, said tubing being also connected to a source of solution capable of use for flushing of a needle track extending through the skin and outer tissue of a patient.

11. The kit of claim 10 in which the minimum outer diameter of the first cannula proximal portion is at least twice the minimum outer diameter of the first cannula distal portion.

12. A cannula for providing predilation and disinfection fluid flow access through the skin of a patient, the cannula comprising:
    a first, substantially rigid cannula having a proximal end, said cannula having a proximal portion adjacent to said proximal end, said proximal portion having an outer diameter of about 1.2 to 2.7 mm, said cannula having a distal portion adjacent to a cannula distal end, said distal portion having an outer diameter of about 0.5 to 1.5 mm, a maximum outer diameter of the distal portion being smaller than a minimum outer diameter of the proximal portion and smaller than an inner diameter of a pre-formed bore receiving the cannula so that a gap is formed between the distal portion outer diameter and the bore, said cannula further defining a frustoconical transition portion between said proximal and distal portions, said cannula providing for dilation and flushing of a needle track within a patient's skin and the cannula being connected to a source of disinfecting solution flowing through the cannula, into the patient, through the gap and into the needle track while the cannula resides therein.

13. The cannula of claim 12 in which said proximal and distal portions are cylindrical.

14. The cannula of claim 12 in which said distal cannula end is blunt.

15. The cannula of claim 12 in which said hub is connected to a length of tubing or a syringe, said tubing or syringe containing disinfectant solution capable of use for flushing of said needle track extending through the skin and outer tissue of a patient.

16. The cannula of claim 12 in which the minimum outer diameter of the first cannula proximal portion is at least twice the minimum outer diameter of the first cannula distal portion.

17. A medical procedure kit which comprises: the cannula of claim 12; a second cannula set which comprises a second cannula for providing access through the skin of a patient, the proximal portion of said first cannula having a minimum outer diameter that is about seventy to one hundred percent of a minimum outer diameter of said second cannula; and packaging for both of said cannulas.

18. The kit of claim 17 in which said second cannula comprises a proximal end connected to a second hub and having a distal end, said second cannula tapering inwardly from the proximal to the distal end.

19. The method of providing access through the skin of a patient for flow communication with a body lumen of a patient, which comprises:
    advancing a first cannula having a blunt forward end through a preformed needle track through the skin of the patient, without significantly cutting tissue of the patient, while dilating at least most of the needle track with the cannula to a diameter that is about 70 to 125 percent of the minimum outer diameter of a subsequent cannula, said first cannula having a distal portion of less outer diameter than a first cannula proximal portion positioned for dilating said needle track, said distal portion penetrating an implanted artificial port without opening a closure valve that closes flow between the port and the body lumen, and including the step of passing flushing liquid through said first cannula, most of which liquid then passes out of the patient through said needle track;
    removing the first cannula; and
    advancing the subsequent cannula through the dilated needle track into flow communication with the patient body lumen, said subsequent cannula being advanced into said flow communication by engagement with said implanted, artificial port.

20. A method of providing access through the skin of a patient for communicating with a body lumen of a patient, which comprises:

advancing a first cannula having a blunt forward end through a preformed needle track through the skin of a patient, without significantly cutting tissue of the patient, while dilating at least most of the needle track with the cannula to a diameter that is about 70 to 125 percent of the minimum diameter of a subsequent cannula;

removing the first cannula; and advancing the subsequent cannula through the dilated needle track into flow communication with the patient body lumen and wherein said first cannula has a distal portion of less outer diameter than a first cannula proximal portion positioned for dilating said needle track, said distal portion penetrating an implanted artificial port without opening a closure valve that separates the port from the body lumen, and including the step of passing flushing liquid through said first cannula, most of said liquid then passing out of the patient through the needle track.

21. A system for providing a disinfected blood flow circuit comprising:

an artificial port having a flow conduit for connection with a body lumen, the flow conduit having a first diameter and a closure member for blocking flow between the port and the body lumen, the closure member openable by a blood-flow circuit cannula having a first diameter at its distal portion sized for opening the closure member and sealing the flow conduit; and a predilation cannula having at its distal portion a second diameter smaller than the first diameter, the predilation cannula inserted through a needle track into the artificial port wherein the closure member remains closed and the flow conduit remains at least partially open and upon injection of a disinfecting fluid into the predilation cannula the fluid may exit through the flow conduit providing flushing and disinfecting of a needle track while the predilation cannula resides therein.

22. The disinfected blood flow circuit system of claim 19 wherein the predilation cannula has an outer diameter that is about 70–125% of the outer diameter of the blood flow cannula.

23. The disinfected blood flow circuit system of claim 19 wherein the predilation cannula includes a portion having a diameter larger than the second diameter.

24. The disinfected blood flow circuit system of claim 19, wherein the predilation cannula is connected to a disinfectant fluid flow source.

25. The disinfected blood flow circuit system of claim 19 wherein the blood flow circuit cannula includes a portion having a fourth diameter less than the first diameter.

26. The disinfected blood flow circuit system of claim 19 wherein the blood flow circuit cannula has a tapered distal end.

* * * * *